United States Patent [19]

Hackler et al.

[11] 4,433,066
[45] Feb. 21, 1984

[54] METHOD FOR THE PREPARATION OF HIGH-CALORIC GASES, PARTICULARLY METHANE, BY MEANS OF A CATALYST FLUIDIZED BED

[75] Inventors: Erich Hackler; Claus Flockenhaus, both of Essen; Werner Lommerzheim, M heim, all of Fed. Rep. of Germany

[73] Assignee: Didier Engineering GmbH, Essen

[21] Appl. No.: 340,738

[22] Filed: Jan. 19, 1982

[30] Foreign Application Priority Data

Jan. 21, 1981 [DE] Fed. Rep. of Germany ....... 3101739

[51] Int. Cl.$^3$ .............................................. C07C 1/04
[52] U.S. Cl. .................................... 518/706; 518/707; 48/196 R
[58] Field of Search .............. 518/706, 707; 48/196 R

[56] References Cited

U.S. PATENT DOCUMENTS

| | | | |
|---|---|---|---|
| 2,481,089 | 9/1949 | Dickinson | 518/706 |
| 2,503,356 | 4/1950 | Sensel et al. | 518/707 |
| 2,506,221 | 5/1950 | Keith | 518/706 |
| 3,967,936 | 7/1976 | Tajbl et al. | 518/706 |
| 3,975,169 | 8/1976 | Gent | 518/706 |

Primary Examiner—Howard T. Mars
Attorney, Agent, or Firm—Toren, McGeady and Stanger

[57] ABSTRACT

A method for the production of high-caloric content gases is disclosed wherein feed gases containing CO and $H_2$ are passed through at least two consecutive catalytic fluidized bed stages having cooling elements wherein, the feed gases being introduced to the first stage under pressure and to the subsequent stages under a pressure which is less than the pressure of the next preceding stage, and the gas produced from each preceding stage is fed to the next stage as a diluting gas. As a result of using the method of the present invention, one can avoid the necessity of compression of the feed gases in the subsequent reaction stages, thereby decreasing the cost as well as the technical difficulties encountered in the process.

2 Claims, 1 Drawing Figure

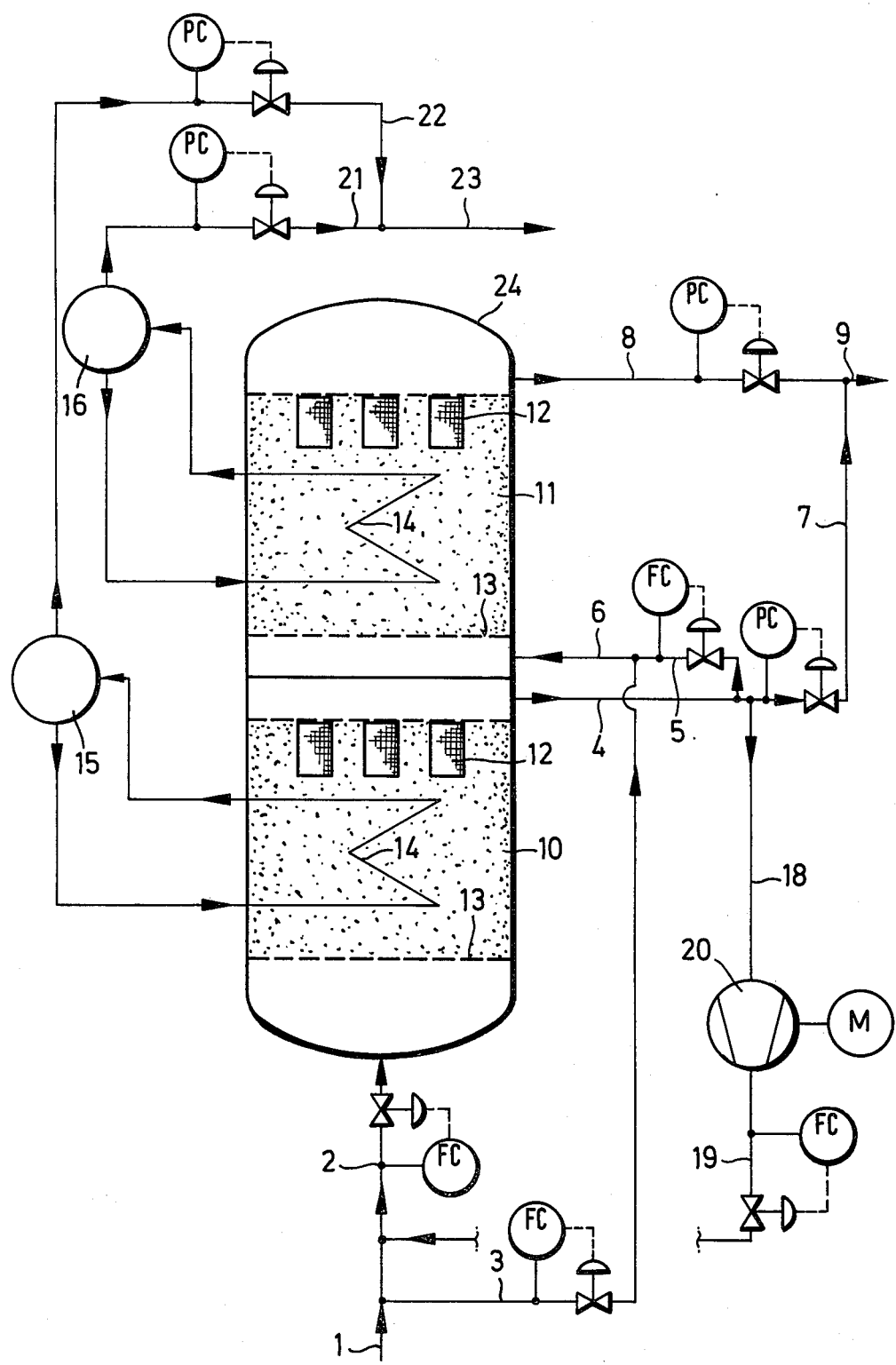

METHOD FOR THE PREPARATION OF HIGH-CALORIC GASES, PARTICULARLY METHANE, BY MEANS OF A CATALYST FLUIDIZED BED

BACKGROUND OF THE INVENTION

1. Field of the Invention

The invention relates to a method for the production of high caloric content gases, particularly methane, by conversion of gases which contain CO and $H_2$ in a fluidized catalytic bed having incorporated cooling elements.

2. Description of the Prior Art

Methods for producing high-caloric content gases and, particularly, methane from low-caloric content gases, such as, hydrogen and carbon oxide, by treatment with a catalyst, in the form of a fluidized bed are well-known.

The output of the fluidized bed units, which operate under pressure, is considerably higher, and the costs are more favorable compared to fixed bed units.

To adjust the feed gases, which may be gases that contain CO and $H_2$ or may be pure gas mixtures of CO and $H_2$, to a specific CO partial pressure and for better adjustment of the heat balance, it is necessary under many conditions to use a so-called cycle gas. This cycle gas is usually fed using compressors and results in high costs as well as great technical difficulties.

SUMMARY OF THE INVENTION

We have discovered a method for reducing and in some cases, minimizing the costs and technical expenditures attendant the use of a cycle gas.

More particularly, we have discovered that this can be accomplished by carrying out the conversion in at least two consecutive fluidized bed stages and wherein the feed gas is introduced to the first stage under pressure and to the subsequent stages under a pressure which is less than the pressure of the preceding stage, and the gas produced from each preceding stage is fed to the next stage as a diluting gas.

When such a fluidized bed having two units, one upper and one lower, is used in the method according to the invention, the lower stage is usually the first stage into which the feed gas is introduced. The lower or first stage is operated with a somewhat higher pressure than the second fluidized bed stage, etc. In this way it becomes possible to conduct a part of the gas produced in the first stage as an addition or diluting gas to the second fluidized bed stage without using a separate compressor. Consequently, the number of compressors as well as the compressor output are reduced.

BRIEF DESCRIPTION OF THE DRAWING

The drawing is a schematic diagram of an embodiment of the inventive method.

DESCRIPTION OF THE PREFERRED EMBODIMENT

In the above-described method, only one cycle compressor is needed for the first stage if the gas produced in the first stage is returned as a diluting agent in the form of a recycled gas to this first stage.

The divided construction of the fluidized bed reactor into individual stages makes it possible to operate the stages with different reaction temperatures. Then, the pressure of the steam cylinder can always be set by means of pressure controllers whereby, for insance, higher vaporization temperatures of the cooling medium can be attained.

By choosing a suitable catalyst, for instance, the first or lower stage can be operated at high reaction temperatures. In a preferred embodiment, a return of produced gas by means of a cycle compressor may be omitted. Setting a favorable, low equilibrium temperature during methanization, i.e., for methane, is then only undertaken in the second fluidized bed stage.

Referring to the drawing, a fluidized bed reactor 24 with two fluidized bed stages 10 and 11 is used. The feed gas, CO and $H_2$ or a gas with high contents of CO and $H_2$, which is needed for a methanization unit is fed through lines 1 and 2 to the fluidized bed stage 10 and through line 3 to the fluidized bed stage 11 while being controlled by means of volume controllers or flow controllers FC. The gases are fed into the individual fluidized bed stages by means of distributor floors 13.

The heat of reaction is removed in the fluidized bed stages 10 and 11 by means of cooling bundles 14. The gas which is produced in stage 10 is conducted by means of lines 4 and 7 to the collecting line 9. By means of line 5, a controlled, reacted gas stream is removed from line 4 and is mixed with the feed gas for the second stage in line 3, so that by means of line 6, a mixture of feed gas and a gas stream which was reacted in stage 10 is introduced at the bottom into the fluidized bed stage 11. Since the pressure in the fluidized bed stage 11 is less than in the fluidized bed stage 10, compression of the feed gas in line 5 is not required.

By adding a part of the reacted gas stream from fluidized bed stage 10 to the feed gas which is introduced into the second stage 11, the conditions for the catalyst in the second stage are less stringent.

The gas which is produced in the fluidized bed stage 11 is fed by means of line 8 to collecting line 9. Filters 12 are arranged ahead of lines 4 and 8, so that only dust-free gas reaches the collecting line 9.

Steam, which is generated in the tube bundles 14 during removal of the heat of reaction, is separated in steam cylinders 15 and 16 and is transported by means of lines 21 and 22 to a steam collecting line 23 for further use.

The first fluidized bed stage 10 in the shown embodiment is equipped with a compressor 20 for the cycle gas. This cycle gas is removed from the first fluidized bed stage 10 via line 4 by means of line 18. After compression in cycle compressor 20, the cycle gas is conducted by means of line 19 to line 2 for feed gas for the first fluidized bed stage 10.

In this way it is possible to set the CO partial pressure of the feed gas which streams through the distributor floor 13 to a desired value. The fluidized bed reactor unit which is used in the method according to the invention may also be distributed over several, completely separate vessels. It is also possible to work with more than two consecutive fluidized bed stages.

The following example wherein a fluidized bed methanization is carried out, illustrates the present invention.

In a fluidized bed unit which is divided into two stages, a feed gas with a pressure of 65 bar and approximately 20° C., as well as an $H_2$:CO ratio of 2.42 was converted to methane by means of a conventional catalyst in the fluidized bed. The feed gas flow in the first stage was approximately 6850 m$^3$/h (N) and the added amount of recycle gas was approximately 2000 m³/h (N). The amount of pure methane gas which was produced in the first stage, calculated as dry gas, was approximately 2000 m³/h (N) with a content of 88 Vol-% $CH_4$. The rest of the gas consisted of $CO_2$, $H_2$ and $N_2$. The same amount of feed gas was fed to the second methanization stage, however, as diluting gas, gas which was produced in the first fluidized bed stage. It was mixed by means of line 5 into line 6 so that 4000 m³/h (N) of pure methane could be removed by means of line 9. The gas was conducted with a pressure of 60 bar by means of line 9 to a drying unit. It can then be supplied with an L-natural gas quality to an existing gas system.

Of course, it is also possible to produce an H-gas quality with the method according to the invention. However, in this case, smaller amounts of nitrogen are necessary in the feed gas. In this case, also a $CO_2$ wash is subsequently carried out.

We claim:

1. In a method for the production of methane wherein feed gases containing CO and $H_2$ are passed through a fluidized catalytic bed having cooling elements therein, the improvement which comprises carrying out the conversion in at least two fluidized bed reactors and wherein the feed gas is introduced to the first reactor under pressure and to the subsequent reactors under a pressure which is less than the pressure of the preceding reactor, a portion of the gas produced in each reactor is fed to a collecting line, another portion of the gas produced from each reactor is fed to the next reactor as a diluting gas and still another portion of the gas produced in the first stage is compressed and returned to the first stage as a recycled diluting gas.

2. The method of claim 1 wherein the gas obtained from the second stage is introduced into the first stage as a diluting gas using a cycle compressor and a portion of the gas from the first stage is introduced into the second stage as a diluting gas.

* * * * *

UNITED STATES PATENT AND TRADEMARK OFFICE
CERTIFICATE OF CORRECTION

PATENT NO.   :   4,433,066
DATED        :   February 21, 1984
INVENTOR(S)  :   Erich Hackler, et al It is certified that error appears in the above-identified patent and that said Letters Patent is hereby corrected as shown below:

In the heading of the Patent [73] should read as follows:

-- [73] Assignees:   Didier Engineering GmbH, Essen
and Thyssengas GmbH, Duisburg,
both of Federal Rep. of Germany --

Signed and Sealed this

Nineteenth Day of June 1984

[SEAL]

Attest:

GERALD J. MOSSINGHOFF

Attesting Officer

Commissioner of Patents and Trademarks